US00PP35971P2

(12) United States Plant Patent
Crane

(10) Patent No.: US PP35,971 P2
(45) Date of Patent: Jul. 9, 2024

(54) APPLE TREE NAMED 'SM102543'

(50) Latin Name: ***Malus domestica* Mill.**
Varietal Denomination: SM102543

(71) Applicant: Prevar Limited, Hastings (NZ)

(72) Inventor: Barclay Crane, Spokane, WA (US)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/085,233

(22) Filed: Dec. 20, 2022

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./156, 161
See application file for complete search history.

(56) References Cited

U.S. PATENT DOCUMENTS

PP22,356 P3 * 12/2011 White ..... A01H 5/08 Plt./161
PP22,546 P3 * 3/2012 Dupont, Sr. ..... A01H 5/02 Plt./257

* cited by examiner

*Primary Examiner* — Karen M Redden
(74) *Attorney, Agent, or Firm* — Michelle Bos Legal LLC

(57) ABSTRACT

An apple tree named 'SM102543' notable for its attractive fruit, which exhibits an intense striped overcolor.

3 Drawing Sheets

Genus and species: *Malus domestica* Mill.
Variety denomination: 'SM102543'.

BRIEF DESCRIPTION OF THE VARIETY

A new apple tree named 'SM102543' was discovered near Quincy, Washington in 2016 as a spontaneous limb sport mutation of a 'PremA17' apple tree (U.S. Plant Pat. No. 22,356) growing in a cultivated orchard of 'PremA17' trees. One limb of the 'PremA17' tree bore fruit that matured earlier and was more intensely colored as compared to the rest of the tree. Asexual propagation by grafting was carried out in 2016 at Quincy, Washington. The variety has since been observed over a number of asexually propagated generations, and has been found to remain true to type.

'SM102543' is distinguished from its parent 'PremA17' and from similar variety 'Gala' (U.S. Plant Pat. No. 3,637) as set forth in Table 1 and Table 2 below.

TABLE 1

Comparison of 'SM102543' to Parent Variety 'PremaA17'

| | 'SM102543' | 'PremA17' |
|---|---|---|
| Pattern of overcolor | Stripe | Stripe and blush |
| Overcolor | Red 53A and greyed-purple 187A stripes at stem end, fading to red 47B stripes at calyx end | Red 45A stripe with red 47B blush |
| Intensity of overcolor | Intense, especially near stem end | Moderate |
| Amount of overcolor | 90%+, concentrated on upper half of fruit | 25% of surface |

TABLE 2

Comparison of 'SM102543' to Similar Variety 'Gala'

| Characteristic | 'SM102543' | 'Gala' |
|---|---|---|
| Pattern of overcolor | Stripe | Solid ground color with broad striped and mottled overcolor |
| Flavor profile | Sweet, sub-acid | Sweet |

BRIEF DESCRIPTION OF THE PHOTOGRAPHS

The accompanying photographs were obtained in 2022 at Quincy, Washington. The trees depicted are five years old.

DETAILED BOTANICAL DESCRIPTION OF THE VARIETY

Figure 1:
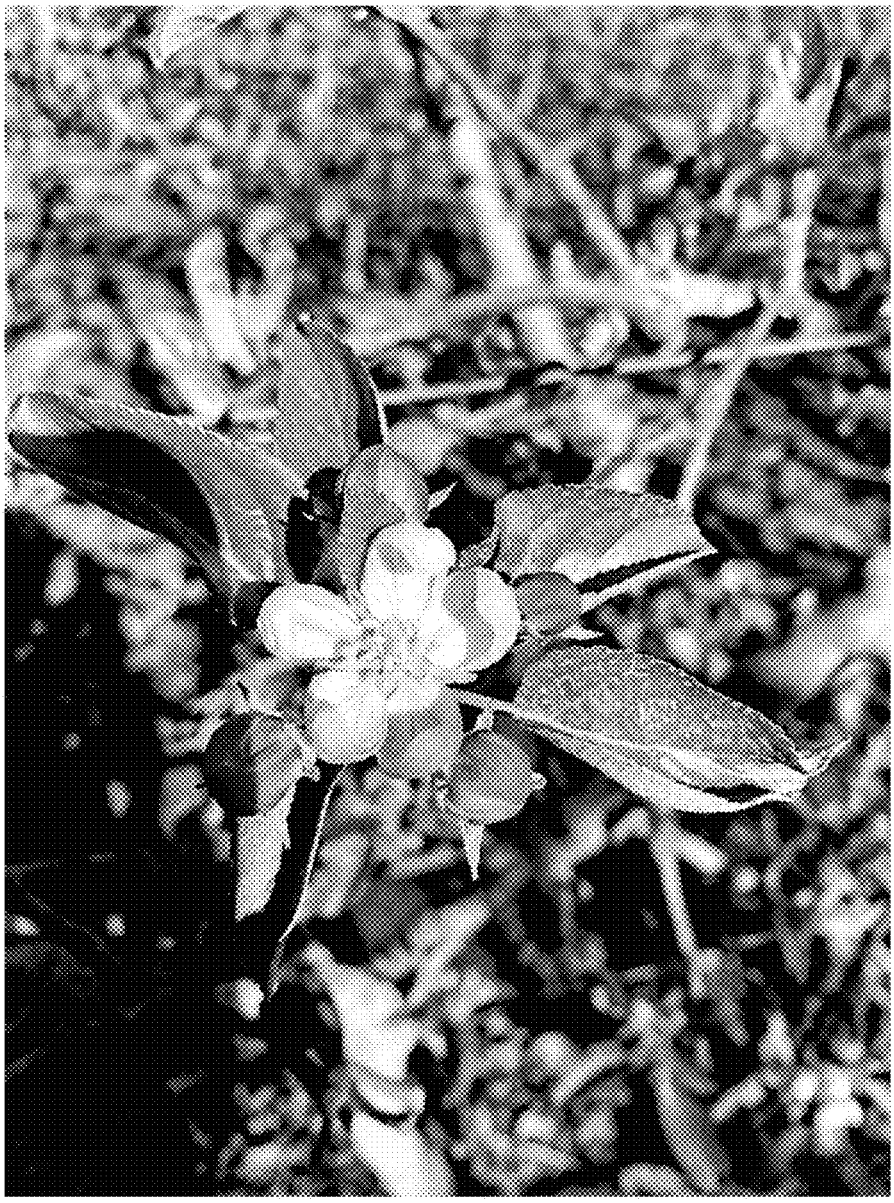
FIG. 1 shows a flower, flower buds and young leaves on a 'SM102543' apple tree.
Figure 2:
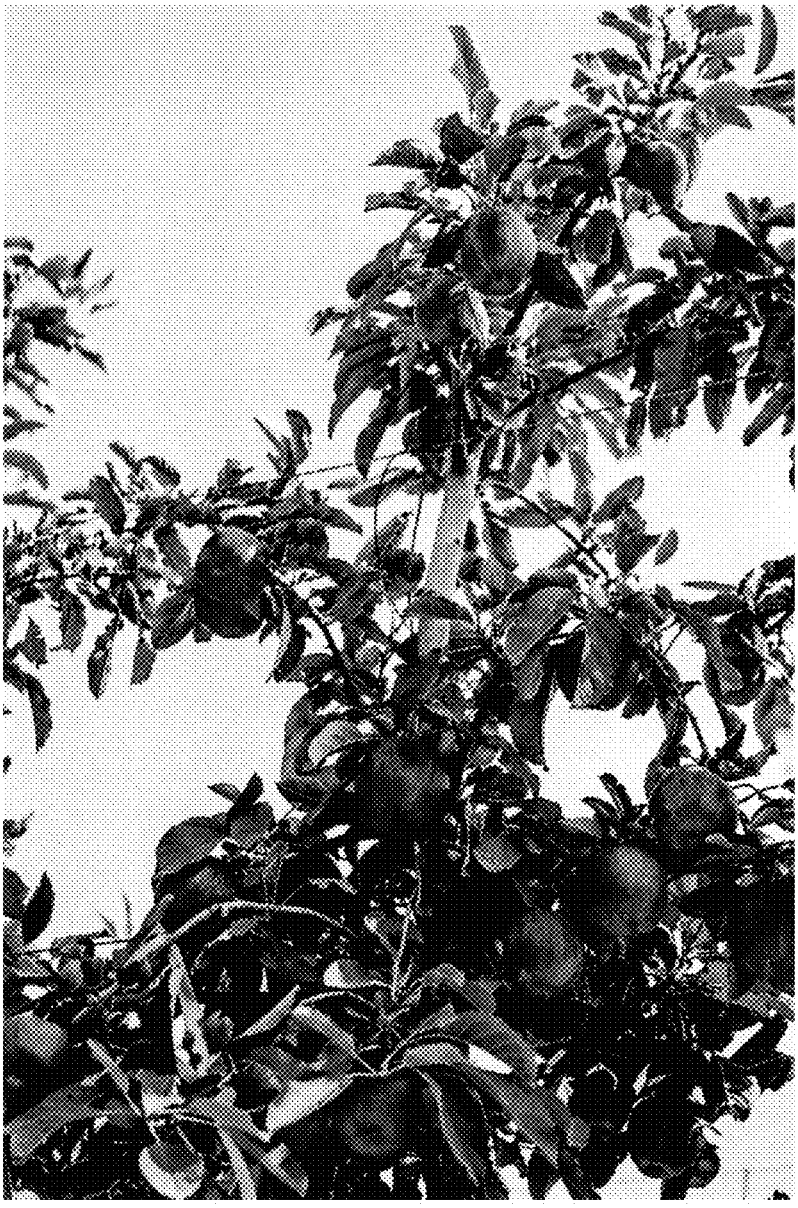
FIG. 2 shows leaves and fruit on a 'SM102543' apple tree.
Figure 3:
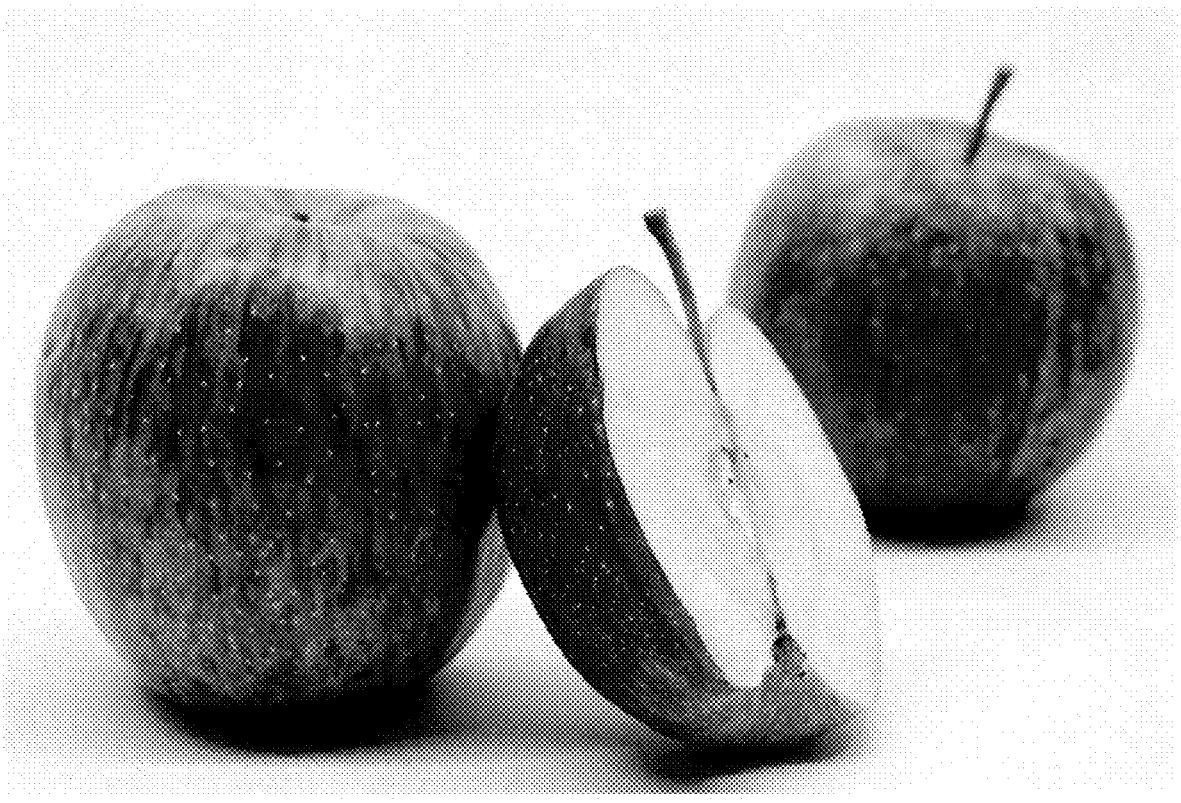
FIG. 3 shows whole and sectioned fruit from a 'SM102543' apple tree.

The following detailed botanical description is based on observations of five-year-old trees growing on 'M9-337' rootstock (not patented), made during the 2022 growing season near Parker, Washington. The described trees are bi-axial and grown on a V-trellis. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor*.—Semi-vigorous.
*Type*.—Columnar.
*Habit*.—Spreading.
*Spread of mature tree*.—About 0.9 m.
*Height*.—About 3.5 m.
*Bearing*.—Spurs and long shoots.
*Trunk diameter*.—6 cm at 30 cm above graft union.
*Bark texture*.—Semi-rough.
*Bark color*.—Brown N200D.
*Lenticel length*.—6 mm.
*Lenticel width*.—2 mm.
*Lenticel shape*.—Elongated.
*Lenticel color*.—Greyed-orange 165C.
*Lenticel density per* $cm^2$.—5 to 6.

Fruiting branches (1 m above graft union):

*Length*.—43 cm.
*Diameter*.—0.5 cm.
*Crotch angle*.—70°.
*Color*.—Brown N200D.
*Lenticel length*.—2 mm.
*Lenticel width*.—1 mm.
*Lenticel shape*.—Elongated.
*Lenticel color*.—White 155D.
*Lenticel density per* 10 $cm^2$.—8 to 10.

One-year-old shoot:

*Length*.—19 cm.
*Diameter*.—0.4 cm.
*Color*.—Brown 199A.
*Internode length*.—3 cm to 4 cm.
*Lenticel length*.—1 mm.
*Lenticel width*.—0.5 mm.
*Lenticel shape*.—Elongated.
*Lenticel color*.—White 155A.
*Lenticel density per* 10 $cm^2$.—12 to 15.

Flowers buds at pre-balloon stage (Apr. 21, 2022):

*Quantity per spur*.—6.
*Bud shape*.—Globose to ovate.
*Apex shape*.—Rounded.
*Length*.—1 cm.
*Diameter*.—0.6 cm.
*Color*.—Red-purple N57B.

Flowers:

*Date of first bloom*.—April 25.
*Date of full bloom*.—April 28.
*Diameter of fully open flower*.—4 cm.

Petals:

*Relative position of petal margins*.—Not touching.
*Quantity per flower*.—5.
*Length*.—2 cm.
*Width*.—1.3 cm.
*Petal shape*.—Ovate.
*Apex shape*.—Rounded.
*Base shape*.—Cuneate.
*Color*.—Upper surface white N155A with red-purple 58D venation; lower surface white N155A with red-purple 58D near apex.
*Petal texture*.—Upper and lower surfaces smooth.
*Petal margin*.—Entire.
*Pistil length*.—1 cm.
*Pistil color*.—Green 142C.
*Style length*.—9 mm.
*Style color*.—Green 142C.
*Stigma diameter*.—1 mm.
*Stigma color*.—Green 142C.
*Ovary length*.—5 mm.
*Ovary color*.—Green 143B.
*Stamen quantity*.—15.
*Filament length*.—6 mm.
*Filament color*.—White 155A.
*Anther length*.—2 mm.
*Anther width*.—1 mm.
*Anther color*.—Yellow 4D.
*Presence of pollen*.—Present, scarce.
*Pollen color*.—Yellow 4D.

Pedicel:

*Length*.—2.5 cm.
*Diameter*.—1 mm.
*Color*.—Green 139D.

Sepals:

*Quantity*.—5.
*Length*.—6 mm.
*Width*.—3 mm at base, tapering to a point.
*Shape*.—Lanceolate.
*Apex shape*.—Acute.
*Margin*.—Entire.
*Color*.—Upper surface — Green 142C.
*Color*.—Lower surface — Yellow-green 145C.

Leaves:

*Length*.—10 cm.
*Width*.—6.5 cm.
*Shape*.—Ovate.
*Apex*.—Acuminate.
*Base*.—Rounded, equilateral.
*Margin*.—Serrate.
*Venation*.—Reticulate.
*Color*.—Upper surface — Green 137A.
*Color*.—Lower surface — Yellow-green N148B.
*Color*.—Veins — Yellow-green 151C.
*Attitude in relation to shoot*.—Downward.

Petiole:

*Length*.—5 cm.
*Diameter*.—2 mm.
*Color*.—Yellow-green 151C.

Fruit:

*Diameter*.—8 cm.
*Height*.—7.5 cm.
*Weight*.—Average 215 g.
*Shape*.—Globose.
*Position of maximum diameter*.—Equator.
*Ribbing*.—Absent.
*Crowning at calyx end*.—Present.
*Aperture of eye*.—Closed.
*Depth of eye basin*.—1.5 cm.
*Diameter of eye basin*.—2.5 cm.
*Stalk length*.—3 cm.
*Stalk diameter*.—4 mm.
*Stalk color*.—Yellow green 145A.
*Depth of stalk cavity*.—1 cm.
*Diameter of stalk cavity*.—1.5 cm.
*Bloom of skin*.—Absent.
*Greasiness of skin*.—Absent.
*Ground color of skin*.—Yellow 1D.
*Over color of skin*.—Red 53A and greyed-purple 187A stripes at stem end, fading to red 47B stripes at calyx end.
*Pattern of overcolor*.—Striped.

*Intensity of overcolor*.—Intense, especially near stem end.
*Amount of overcolor*.—90%+, concentrated on upper half of fruit.
*Lenticel shape*.—Round.
*Lenticel diameter*.—1 mm.
*Lenticel density*.—20 per square inch.
*Lenticel color*.—White 158A.
*Flesh color*.—White 155B.
*Flesh firmness*.—Firm, 11 kg/cm$^2$.
*Flesh texture*.—Crunchy, crisp.
*Juiciness*.—Very juicy.
*Brix*.—15°.

Seeds:

*Quantity per fruit*.—Few, usually 3 to 6.
*Length*.—7 mm.
*Width*.—4 mm.
*Shape*.—Ovate.
*Color*.—Greyed-orange 165A.
*Locule length*.—15 mm.
*Locule width*.—5 mm.
*Quantity of locules per fruit*.—6.
*Harvest date*.—Sep. 20, 2022, second pick about one week later (2022 harvest was two weeks later than typical harvest).
*Number of picks*.—Two.
*Harvest yield*.—9 kg to 11 kg from trees described; yield will vary substantially depending on multiple factors.
*Disease/pest resistance*.—None observed.
*Disease/pest susceptibility*.—None noted.
*Market use*.—Fresh, juice processing.

The invention claimed is:

1. A new and distinct variety of apple tree named 'SM102543', substantially as illustrated and described herein.

* * * * *